Figure 1:
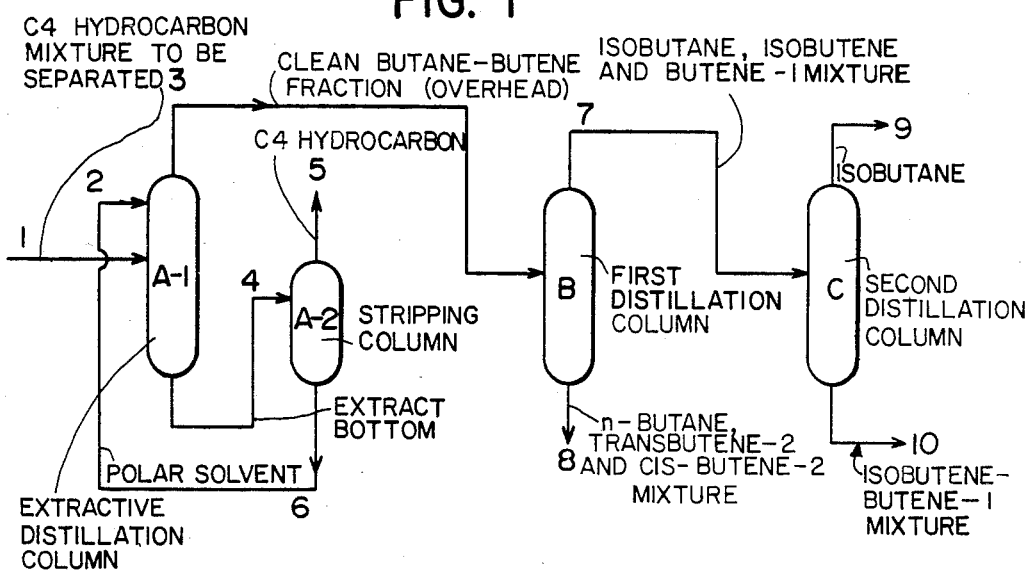

United States Patent [19]

Ogura

[11] Patent Number: 4,555,312
[45] Date of Patent: Nov. 26, 1985

[54] PROCESS FOR SEPARATING HIGHLY PURE BUTENE-1 OR BUTENE-1/ISOBUTENE MIXTURE FROM $C_4$ HYDROCARBON FRACTION

[75] Inventor: Shunichiro Ogura, Tokyo, Japan; Masamichi Soumai, Yokohoma, Japan.

[73] Assignee: Nippon Zeon Co. Ltd., Tokyo, Japan

[21] Appl. No.: 444,039

[22] Filed: Nov. 23, 1982

[30] Foreign Application Priority Data

Nov. 27, 1981 [JP] Japan ............................ 56-190385

[51] Int. Cl.⁴ .............................................. C07C 7/08
[52] U.S. Cl. .......................... 203/29; 203/38; 203/45; 203/60; 203/81; 585/809; 585/860; 585/864
[58] Field of Search ................ 203/60, 50, 45, 74, 203/81; 585/800, 809, 810, 860, 864; 568/697, 699

[56] References Cited

U.S. PATENT DOCUMENTS

| | | | |
|---|---|---|---|
| 2,911,452 | 11/1959 | Broughton | 585/809 |
| 3,121,124 | 2/1964 | Verdol | 585/864 |
| 3,170,000 | 2/1965 | Verdol | 585/864 |
| 3,232,849 | 2/1966 | Renberg | 203/78 X |
| 3,232,850 | 2/1966 | Renberg et al. | 203/78 X |
| 3,772,158 | 11/1973 | Sarno | 203/62 X |
| 3,795,588 | 3/1974 | Preusser et al. | 203/73 X |
| 4,269,668 | 5/1981 | Patel | 203/84 |
| 4,356,339 | 10/1982 | Imaizumi et al. | 585/811 X |
| 4,391,677 | 7/1983 | Harris et al. | 203/41 |
| 4,448,643 | 5/1984 | Lindner et al. | 203/71 |

Primary Examiner—Wilbur Bascomb
Attorney, Agent, or Firm—Sherman & Shalloway

[57] ABSTRACT

A process for separating a butene-1/isobutene mixture from a $C_4$ hydrocarbon fraction is provided which comprises subjecting the $C_4$ hydrocarbon fraction to extractive distillation using a polar solvent to separate components predominantly containing 1,3-butadiene as an extract bottom and obtain an overhead containing butanes, butene-1, isobutene and butene-2 as main components and being substantially free from $C_3$-$C_4$ diolefinic and acetylenic hydrocarbons, feeding the overhead into a first distillation column, removing n-butane and butene-2 as bottoms from the column, feeding low-boiling components from the top of the column into a second distillation column, removing isobutane from the top of the second distillation column, and obtaining highly pure butene-1 and isobutene from its bottom. When isobutene contained in the overhead in the above process is removed in the form of tertiary butyl alcohol or tertiary butyl ether before it is fed into the first distillation column, highly pure butene-1 alone is obtained from the bottom of the second distillation column.

6 Claims, 2 Drawing Figures

PROCESS FOR SEPARATING HIGHLY PURE BUTENE-1 OR BUTENE-1/ISOBUTENE MIXTURE FROM C4 HYDROCARBON FRACTION

This invention relates to a process for separating highly pure butene-1 or a mixture of butene-1 and isobutene from a $C_4$ hydrocarbon fraction.

It is an object of this invention to obtain large quantities of 1,3-butadiene, isobutene, and butene-1 which is highly pure as to be usable as a starting material for polymers and is free from hazardous impurities at low cost from a $C_4$ hydrocarbon fraction, for example a $C_4$ hydrocarbon fraction formed as a by-product in the steam cracking of naphtha.

We have found that the above object of this invention is achieved by treating a $C_4$ hydrocarbon fraction having a similar composition to that illustrated in Table 1 below by a process comprising a combination of an extractive distillation step using a polar solvent, particularly dimethylformamide, and an ordinary distillation step, and as a result, there can be obtained butene-1 and isobutene substantially free from diolefinic and acetylenic hydrocarbons and water which are detrimental to the use of these butenes as a comonomer for ethylene polymerization or as a monomer for butene-1 polymerization, and at the same time 1,3-butadiene containing small amounts of acetylenes can be obtained.

TABLE 1

| Composition of O4 hydrocarbon fraction | | |
|---|---|---|
| Component | Boiling point (°C.) | Proportion % |
| Propane | −42.1 | 0.08 |
| Propylene | −47.7 | 0.07 |

According to the process of this invention, there is provided a process which comprises subjecting a $C_4$ hydrocarbon fraction having a similar composition to that illustrated in Table 1 to extractive distillation using a polar solvent to separate it into a butane-butene $C_4$ hydrocarbon fraction composed of isobutane, n-butane, butene-1, isobutene, trans-butene-2- and cis-butene-2 and being substantially free from 1,3-butadiene and acetylenes (to be referred to as an overhead or a clean butane-butene fraction) and butadienes containing 1,3-butadiene and small amounts of acetylenes (to be referred to as an extract bottom or crude butadiene); thereafter, subjecting the overhead or clean butane-butene fraction to a first distillation step to obtain a mixture of isobutane, isobutene and butene-1 from the top of the distillation column and a mixture of n-butane, trans-butene-2 and cis-butene-2 from its bottom; and thereafter, subjecting the mixture of isobutane, isobutene and butene-1 from the top of the column to a second distillation step to obtain isobutane from the top of the second distillation column and a mixture of isobutene and butene-1 from its bottom.

Since butene-1 and isobutene have close boiling points, it is virtually impossible to separate them from their mixture by the aforesaid distillation. iso-Butene, however, can be separated by converting it to tertiary butyl alcohol by a recently developed hydration reaction using acidic ion exchange resin as a catalyst, or to tertiary butyl ether by a recently developed etherification reaction with an aliphatic alcohol using the aforesaid acid catalyst. For example, according to the paper of A. Clementi of ASSORENI Company of Italy (Hydrocarbon Processing, December 1979, pages 109–113) and the paper of T. Floris et al. of the same company (SNAMPROGETTI/ANIC MTBE PROCESS BENEFITS UNLEADED GASOLINE REFINERS, at the 1979 NPRA Annual Meeting), when a mixture of a $C_4$ hydrocarbon fraction and methanol is contacted with an acid catalyst (for example, an ion exchange resin having sulfo groups), isobutene is etherified almost completely, and its concentration in the $C_4$ hydrocarbon fraction is reduced to less than 0.1%.

A reaction apparatus for the above hydration reaction or etherification is preferably provided between the extractive distillation column and the distillation column. In this case, water, alcohol, etc. formed in these reaction steps may be removed in the subsequent distillation step.

Since butene-1 obtained by the process of this invention is of high purity as illustrated in Table 2 below, it can be used as a comonomer for ethylene polymerization, or as a material for obtaining polybutene-1 by its own polymerization. This polymer has excellent properties, such as high resistance to stress cracking at high temperatures, high resistance to creep at high temperatures and high resistance to environmental stress cracking, and is suitable as a material for hot water pipes in heater systems.

TABLE 2

| Composition of butene-1 | |
|---|---|
| Butene-1 | more than 99.0% by weight |
| Butene-2 | less than 0.5% by weight |
| iso-Butene | less than 0.5% by weight |
| n-Butane | less than 0.5% by weight |
| 1,3-Butadiene | less than 150 ppm |
| Acetylenes | less than 15 ppm |
| Water | less than 10 ppm |

The extract of the extractive distillation (crude butadiene) which consists mainly of 1,3-butadiene contains methylacetylene, vinylacetylene, ethylacetylene and 1,2-butadiene as impurities. By removing these impurities by selective hydrogenation, or by extractive distillation using a polar solvent, highly pure 1,3-butadiene can be obtained.

The polar solvent used in this invention may be any polar solvents which are used in the separation of 1,3-butadiene from a $C_4$ hydrocarbon fraction by extractive distillation. Examples include N-alkylated lower fatty acid amides, furfural, β-methoxypropionitrile, N-methyl pyrrolidone, formylmorpholine and acetonitrile.

Specific examples of the N-alkylated lower fatty acid amides are dimethylformamide, diethylformamide, and dimethylacetamide. These polar solvents in an anhydrous condition are suitable for the object of this invention since they have an excellent solubility, an excellent relative volatility and a moderate boiling point. Table 3 shows the relative volatilities of $C_4$ hydrocarbons in various polar solvents. Among these solvents, dimethylformamide is most preferred because it has a moderate boiling point and an excellent relative volatility.

These polar solvents may be used singly or in combination with each other. Or they may be mixed with a suitable amount of water, methanol, etc. in order to adjust their boiling points.

The polar solvents may also be used in admixture with a polymerization inhibitor for inhibiting the polymerization of diolefinic or acetylenic hydrocarbons, an antioxidant, an antifoamer, etc. The polymerization inhibitor may be any compound which has the ability to inhibit polymerization and/or induce chain transfer. Preferred polymerization inhibitors include t-butylcatechol, sulfur, sodium nitrite, furfural, benzaldehyde, and aromatic nitro compounds to be used either singly or in combination with each other.

TABLE 3

Relative volatilities of various polar solvents (data obtained at 50° C. with infinite dilution)

| Solvent | Dimethyl-formamide | Diethyl-formamide | N—methyl-pyrrolidone |
| --- | --- | --- | --- |
| Boiling point (°C.) | 153 | 177.5 | 202 |
| C$_4$ Hydrocarbons |  |  |  |
| iso-Butane | 5.3 | 5.2 | 7.25 |
| n-Butane | 3.8 | 3.6 | 4.30 |
| Butene-1 | 2.4 | 2.3 | 2.60 |
| trans-Butene-2 | 1.9 | 1.8 | 2.00 |
| cis-Butene-2 | 1.7 | 1.5 | 1.63 |
| 1,3-Butadiene | 1.0 | 1.0 | 1.00 |
| Methylacetylene | 0.95 | 0.96 | 0.96 |
| 1,2-Butadiene | 0.53 | 0.55 | 0.53 |
| Ethylacetylene | 0.40 | 0.43 | 0.41 |
| Vinylacetylene | 0.24 | 0.29 | 0.18 |

Figure 2:
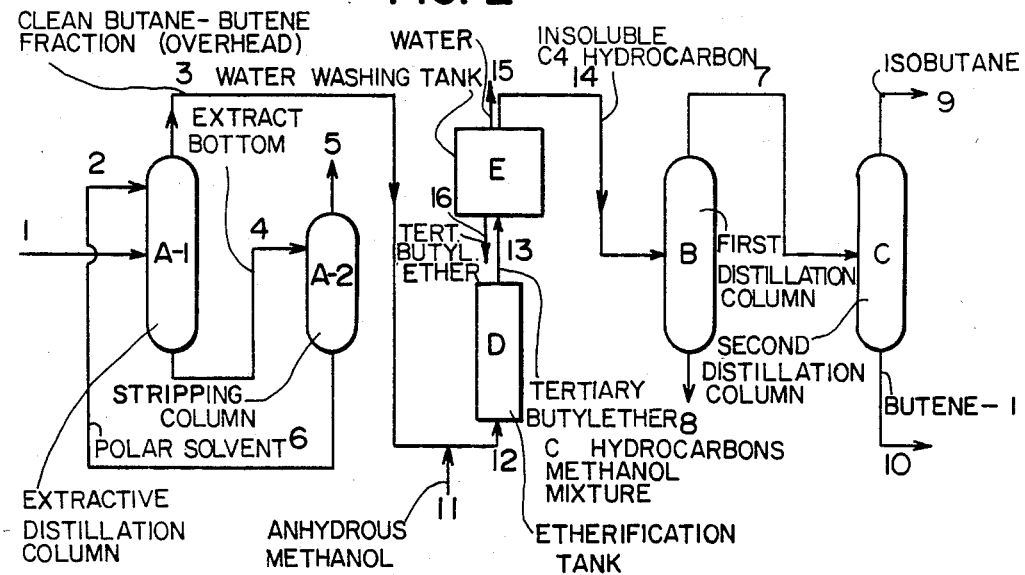

The preferred embodiments of the present invention are described below with reference to the accompanying drawings in which FIGS. 1 and 2 are flow sheets showing two different examples of the process for separation in accordance with this invention.

In these drawings, A-1 represents an extractive distillation column; A-2, a stripping column; B, a first distillation column; C, a second distillation column; D, an etherification tank; and E, a water washing tank.

According to the embodiment shown in FIG. 1, a C$_4$ hydrocarbon fraction containing butene-1, isobutene and 1,3-butadiene is fed through a line 1 into the middle of the extractive distillation column A-1 having 200 trays (consisting of two series-connected column units each having 100 trays), and extractively distilled while a polar solvent is being fed through a line 2 into that part of the column which is several trays below the top of the column. From the top of the column, a C$_4$ hydrocarbon mixture consisting of isobutane, n-butane, butene-1, isobutene, trans-butene-2 and cis-butene-2 is obtained through a line 3. This mixture is a clean butane-butene fraction substantially free from 1,3-butadiene or acetylenes. This extractive distillation can be operated at a column pressure of 1 to 15 atmospheres and a column bottom temperature of 100° to 180° C. From the bottom of the extractive distillation column, 1,3-butadiene and acetylenic and diolefinic hydrocarbons are withdrawn together with the solvent, and fed through a line 4 into the top of the stripping column A-2 where they are separated into C$_4$ hydrocarbons and the polar solvent. The operation in the stripping column is usually performed while maintaining the pressure of the inside of the column at 1 to 2 atmospheres and the temperature of its bottom at the boiling point of the solvent at the operating pressure.

From the top of the stripping column A-2, 1,3-butadiene and acetylenic and diolefinic hydrocarbons are withdrawn through a line 5. From the bottom of the stripping column, only the solvent is withdrawn and recycled to the column A-1 through a line 6.

The clean butane-butene fraction is fed through the line 3 into the middle of distillation column B having 100 trays. The distillation column B can be operated while maintaining the pressure of the inside of the column at 1 to 15 atmospheres and the temperature of the inside of the column at the boiling point of the hydrocarbon mixture at the operating pressure. A mixture of isobutane, isobutene and butene-1 is withdrawn from the top of the distillation column B through a line 7, and then fed into the middle of the next distillation column C having 100 trays. From the bottom of the distillation column B, a mixture of n-butane, trans-butene-2 and cis-butene-2 is withdrawn through a line 8.

Distillation at the distillation column C can be carried out while maintaining the pressure of the inside of the column at 1 to 15 atmospheres and the temperature of the inside of the column at the boiling point of the hydrocarbon mixture at the operating pressure. From the top of the column C, isobutane is withdrawn through a line 9, and from its bottom, a highly pure mixture of isobutene and butene-1 which does not substantially contain butadiene and acetylenic and diolefinic hydrocarbons is withdrawn through a line 10.

In the process of the embodiment shown in FIG. 2, the operations of the extractive distillation column A-1 and the stripping column A-2 are the same as described above with reference to FIG. 1. However, in the process of this embodiment, the clean butane-butene fraction discharged from the line 3 is mixed with anhydrous methanol sent from a line 11 and enters the etherifying tank D. The etherifying tank D is filled with particles of an acidic ion exchange resin, and isobutene reacts there with methanol to form tertiary butyl ether. In order to react isobutene completely, methanol is desirably present in excess. The resulting mixture of tertiary butyl ether, C$_4$ hydrocarbons and the unreacted methanol is fed into the water washing tank E through a line 13, and contacted there with a large amount of water from line 15, whereby tertiary butyl ether and methanol are dissolved in water and removed via line 16. The C$_4$ hydrocarbons insoluble in water are sent through a line 14 to the distillation column B. The operations of the distillation column B and the distillation column C are the same as described above with reference to FIG. 1.

The following non-limitative Examples illustrate the present invention.

EXAMPLE 1

The following experiment was conducted in an apparatus of the type shown in FIG. 1.

A starting material having the composition shown in Table 4 below was fed at a rate of 50 kg/hour into the middle of extractive distillation column A-1 having 200 trays, and extractively distilled while feeding a polar solvent at a rate of 400 kg/hour and passing the reflux liquid at a rate of 60 kg/hour. The extractive distillation column was operated at a column top pressure of 3.0 kg/cm$^2$.G, a column top temperature of 35° C. and a column bottom temperature of 145° C. As a result, a clean butane-butene fraction substantially free from 1,3-butadiene and acetylenic and diolefinic hydrocarbons was obtained at a rate of 29.1 kg/hour from the top of the extractive distillation column A-1. From the top of the stripping column, crude butadiene was obtained at a rate of 20.9 kg/hour.

The clean butane-butene fraction (29.1 kg/hour) was fed into the middle of the distillation column B having 100 trays, and distilled at a reflux ratio of 40, a column top pressure of 3.3 kg/cm$^2$.G, and a column top temperature of 37° C. As a result, a mixture of butene-2 and n-butane was obtained from the bottom of the column at a rate of 9.4 kg/hour.

From the top of the distillation column B, a mixture of isobutane, isobutene and butene-1 was obtained. It was entirely fed into the middle of distillation column C having 100 trays. The distillation column C was operated at a reflux ratio of 150, a column top pressure of 4.0 kg/cm$^2$.G and a column top temperature of 40° C. As a result, a fraction containing isobutane as a main component was distilled off from the top of the column C at a rate of 2.6 kg/hour. From the bottom of the column C, a mixture of isobutene and butene-1 which was highly pure and did not substantially contain 1,3-butadiene and acetylenic and diolefinic hydrocarbons was obtained at a rate of 17 kg/hour.

The compositions of the products at various sites in the process are shown in Table 4.

The polar solvent used consisted of anhydrous dimethylformamide containing 0.1% by weight of nitrobenzene and 0.05% by weight of sodium nitrite.

TABLE 4

| Components | Starting C$_4$ hydrocarbons (from line 1) | Crude butadiene (from line 5) | Clean butane-butene fraction (from line 3) | Butene-2 and n-butane (from line 8) | iso-Butane (from line 9) | iso-Butene and butene-1 (from line 10) |
| --- | --- | --- | --- | --- | --- | --- |
| iso-Butane | 2.50% | — | 4.30% | — | 45.9% | 0.23% |
| n-Butane | 8.61 | — | 14.81 | 45.25% | — | 0.17 |
| Butene-1 | 14.52 | — | 24.98 | 1.95 | 19.3 | 38.66 |
| iso-Butene | 23.22 | — | 39.96 | 4.05 | 34.8 | 60.76 |
| trans-Butene-2 | 6.17 | 0.43% | 10.31 | 31.50 | — | 0.12 |
| cis-Butene-2 | 4.08 | 1.91 | 5.64 | 17.25 | — | 0.06 |
| 1,3-Butadiene | 39.68 | 94.74 | 30 ppm | 10 ppm | — | 35 ppm |
| Methylacetylene | 0.04 | 0.10 | not detected | not detected | — | not detected |
| 1,2-Butadiene | 0.29 | 0.69 | " | " | — | |
| Ethylacetylene | 0.18 | 0.43 | " | " | — | |
| Vinylacetylene | 0.71 | 1.70 | " | " | — | |
| | 100.00 | 100.00 | 100.00 | 100.00 | 100.00 | 100.00 |

Referential Example

Using the same material and apparatus as used in Example 1, extractive distillation was carried out under the following conditions.

Amount of the material fed: 50 kg/hour
Amount of the polar solvent fed: 300 kg/hour
Amount of the reflux liquid: 45 kg/hour From the top of the extractive distillation column A-1, a butane-butene fraction having the composition described in Table 5 was obtained at a rate of 29.4 kg/hour. This fraction was distilled under the same conditions as in Example 1 in the distillation columns B and C, and butene-1 was obtained from the bottom of the distillation column C at a rate of 117.1 kg/hour. The butene-1 contained 0.51% of 1,3-butadiene.

The compositions of these products are shown in Table 5.

The polar solvent used was the same as in Example 1.

TABLE 5

| Component | Butane-butene fraction (from line 3) | iso-Butene and butene-1 (from line 10) |
| --- | --- | --- |
| iso-Butane | 4.25% | 0.23% |
| n-Butane | 14.63 | 0.18 |
| Butene-1 | 24.67 | 38.46 |
| iso-Butene | 39.43 | 60.44 |
| trans-Butene-2 | 10.47 | 0.12 |
| cis-Butene-2 | 6.25 | 0.06 |
| 1,3-Butadiene | 0.30 | 0.51 |
| Methylacetylene | 100 ppm | not detected |
| 1,2-Butadiene | not detected | " |

TABLE 5-continued

| Component | Butane-butene fraction (from line 3) | iso-Butene and butene-1 (from line 10) |
| --- | --- | --- |
| Ethylacetylene | " | " |
| Vinylacetylene | " | " |
| | 100.0 | 100.0 |

EXAMPLE 2

The following experiment was conducted using an apparatus of the type shown in FIG. 2 (the etherifying tank D and water washing tank E were provided between the extractive distillation column A-1 and the distillation column B in the apparatus of FIG. 1).

A clean butane-butene fraction (10.0 kg/hour) obtained under the same conditions as in Example 1 was mixed with anhydrous methanol (25 kg/hour) at a mole ratio of 1:1.1, and the mixture was fed into a cylindrical reactor D filled with about 300 liters of beads of Amberlite 15 (an ion exchange resin having sulfo groups) and kept at about 60° C. to perform etherification. The resulting mixture of tertiary butyl ether, C$_4$ hydrocarbons and the unreacted methanol was fed into the washing tank E containing 2,000 liters of water to remove tertiary butyl ether and the unreacted methanol as an aqueous layer.

The butene fraction from which isobutene had been thus removed was fed into the middle of distillation column B having 100 trays at a rate of 20.0 kg/hour, and distilled at a reflux ratio of 50, a column top pressure of 3.4 kg/cm$^2$.G and a column top temperature of 37° C. As a result, a mixture of butene-2 and n-butane was obtained from the bottom of the distillation column B at a rate of 11 kg/hour. From the top of the distillation column B, a mixture of isobutane and butene-1 was obtained. The mixture of isobutane and butene-1 was entirely fed into the middle of distillation column C having 100 trays, and distilled at a reflux ratio of 130, a column top pressure of 4.0 kg/cm$^2$.G and a column top temperature of 37° C. From the bottom of the distillation column C, a fraction containing isobutane as a main component was distilled off at a rate of 1.5 kg/hour, and from the bottom of the column C, highly pure butene-1 substantially free from 1,3-butadiene and acetylenic and diolefinic hydrocarbons was obtained at a rate of 7.5 kg/hour. Tertiary butyl ether, methanol and water were not detected.

The compositions of the products are shown in Table 6.

TABLE 6

| Component | Clean butane-butene fraction (from line 3) | Butene fraction after removing isobutene (from line 14) | Butene-1 (from line 10) |
| --- | --- | --- | --- |
| iso-Butane | 4.3% | 7.15% | 0.10% |
| n-Butane | 14.81 | 24.63 | 0.12 |
| Butene-1 | 24.98 | 41.54 | 99.22 |
| iso-Butene | 39.96 | 0.15 | 0.40 |
| trans-Butene-2 | 10.31 | 17.15 | 0.11 |
| cis-Butene-2 | 5.64 | 9.38 | 0.05 |
| 1,3-Butadiene | 30 ppm | 40 ppm | 95 ppm |
|  | 100.0 | 100.0 | 100.0 |

What we claim is:

1. A process for separating a butene-1/isobutene mixture from a $C_4$ hydrocarbon fraction, which comprises subjecting the $C_4$ hydrocarbon fraction to extractive distillation using a polar solvent to separate components predominantly containing 1,3-butadiene as an extract bottom and obtain an overhead containing butanes, butene-1, isobutene and butene-2 as main components and being substantially free from $C_3$–$C_4$ diolefinic and acetylenic hydrocarbons, feeding the overhead into a first distillation column, removing n-butane and butene-2 as bottoms from the column, feeding low-boiling components from the top of the column into a second distillation column, removing isobutane from the top of the second distillation column, and obtaining highly pure butene-1 and isobutene from its bottom.

2. The process of claim 1 wherein the polar solvent is dimethylformamide.

3. A process for separating butene-1 from a $C_4$ hydrocarbon fraction, which comprises subjecting the $C_4$ hydrocarbon fraction to extractive distillation using a polar solvent to separate components predominantly containing 1,3-butadiene as an extract bottom and obtain an overhead containing butanes, butene-1, isobutene and butene-2 as main components and being substantially free from $C_3$–$C_4$ diolefinic and acetylenic hydrocarbons, converting isobutene to tertiary butyl alcohol by hydration or to tertiary butyl ether by etherification, removing isobutene as tertiary butyl ether by etherification, removing isobutene as tertiary butyl alcohol or tertiary butyl ether from the overhead, then feeding the remainder of the overhead into a first distillation column, removing n-butane and butene-2 as bottoms from the column, feeding low-boiling components from the top of the column into a second distillation column, removing isobutane from the top of the second distillation column, and obtaining highly pure butene-1 from its bottom.

4. The process of claim 3 wherein the polar solvent is dimethylformamide.

5. The process of claim 3 wherein isobutene is converted to tertiary butyl alcohol by hydration.

6. The process of claim 3 wherein isobutene is converted to tertiary butyl ether by etherification.

* * * * *

UNITED STATES PATENT AND TRADEMARK OFFICE
CERTIFICATE OF CORRECTION

PATENT NO. : 4,555,312
DATED : November 26, 1985
INVENTOR(S) : SHUNICHIRO OGURA, ET AL.

It is certified that error appears in the above-identified patent and that said Letters Patent is hereby corrected as shown below:

IN THE CLAIMS

Claim 3, lines 11-12, (column 8, lines 15-16), delete "removing isobutene as tertiary butyl ether by etherification,".

Signed and Sealed this

Fourth Day of February 1986

[SEAL]

Attest:

DONALD J. QUIGG

Attesting Officer

Commissioner of Patents and Trademarks